United States Patent [19]

Plikaytis et al.

[11] Patent Number: 5,652,106
[45] Date of Patent: Jul. 29, 1997

[54] RAPID AMPLIFICATION-BASED SUBTYPING OF MYCOBACTERIUM TUBERCULOSIS

[75] Inventors: Bonnie B. Plikaytis, Tucker; Thomas M. Shinnick, Atlanta; Jack T. Crawford, Dunwoody, all of Ga.

[73] Assignee: The United States of America as represented by the Secretary of the Department of Health and Human Services, Washington, D.C.

[21] Appl. No.: 548,199

[22] Filed: Oct. 25, 1995

Related U.S. Application Data

[63] Continuation of Ser. No. 327,065, Oct. 19, 1994, abandoned, which is a continuation of Ser. No. 72,450, Jun. 4, 1993, abandoned.

[51] Int. Cl.$^6$ .................................................. C12Q 1/68
[52] U.S. Cl. ..................... 435/6; 435/91.2; 435/91.52; 536/24.32
[58] Field of Search .................... 536/22.1, 24.32; 435/6, 91.2

[56] References Cited

U.S. PATENT DOCUMENTS 5,168,039  12/1992  Crawford et al. .................... 435/6

OTHER PUBLICATIONS

Plikajtis et al. Multiple PCR Assay Specific for the Multidrug-Resistance Strain w of *Mycobacterium Tuberculosis*, J. Clin. Microbiology, 1994, 32(6), pp. 1542–1546.

Edlin, et al., "An Outbreak of Multidrug–Resistant Tuberculosis Among Hospitalized Patients With the Acquired Immunodeficiency Syndrome," *The New England Journal of Medicine* 326(23):1514–1521 (Jun. 4, 1992).

Hermans, et al., "Characterization of a Major Polymorphic Tandem Repeat in *Mycobacterium tuberculosis* and its Potential Use in the Epidemiology of *Mycobacterium kansasii* and *Mycobacterium gordonae*," *Journal of Bacteriology* 174(12):4157–4165 (Jun. 1992).

Cousins, et al., "Use of Polymerase Chain Reaction for Rapid Diagnosis of Tuberculosis," *Journal of Clinical Microbiology* 30(1):255–258 (Jan. 1992).

Otal, et al., "Restriction Fragment Length Polymorphism Analysis Using IS110 as an Epidemiological Marker in Tuberculosis," *Journal of Clinical Microbiology* 29(6):1252–1254 (Jun. 1991).

Cave, et al., "IS6110: Conservation of Sequence in the *Mycobacterium tuberculosis* Complex and its Utilization in DNA Fingerprinting," *Molecular and Cellular Probes* 5:73–80 (1991).

Versalovic, et al., "Distribution of Repetitive DNA Sequences in Eubacteria and Application to Fingerprinting of Bacterial Genomes," *Nucleic Acids Research* 19(24):6823–6831 (1991).

Thomas M.Shinnick, "The 65–Kilodalton Antigen of *Mycobacterium tuberculosis*,"*Journal of Bacteriology* 169(3):1080–1088 (Mar. 1987).

*Primary Examiner*—Kenneth R. Horlick
*Assistant Examiner*—Joyce Tung
*Attorney, Agent, or Firm*—Jones & Askew

[57] ABSTRACT

The present invention provides methods of detecting or distinguishing the DNA of an individual strain of *Mycobacterium tuberculosis* utilizing the polymerase chain reaction (PCR). Reproducible, unique patterns can be produced allowing the identification of unknown *M. tuberculosis* DNA by performing this reaction and comparing the pattern produced to the known reproducible, unique patterns. The invention further provides a kit useful to detect or distinguish the DNA of an individual strain of *M. tuberculosis* in a sample, comprising specific primers for use in PCR. The present invention also provides a method of determining the presence of a multidrug-resistant *M. tuberculosis* by detecting the presence of a specific arrangement of genomic DNA. Such detection can be done using PCR or a ligase chain reaction (LCR). The present invention provides nucleic acid sequences useful in detecting multidrug-resistant *M. tuberculosis*.

14 Claims, 2 Drawing Sheets

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Mycobacterium ( v i i ) IMMEDIATE SOURCE:
        ( B ) CLONE: IS56

( v i i i ) POSITION IN GENOME:
        ( A ) CHROMOSOME/SEGMENT: Insertion element IS6110
        ( B ) MAP POSITION: 170-151 (Thierry et al., (1990))

( x i ) SEQUENCE DESCRIPTION: SEQ ID NO:1:

GCGACCTCAC TGATCGCTGC        20

( 2 ) INFORMATION FOR SEQ ID NO:2:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Mycobacterium ( v i i ) IMMEDIATE SOURCE:
        ( B ) CLONE: MPTR-1

( v i i i ) POSITION IN GENOME:
        ( A ) CHROMOSOME/SEGMENT: MPTR-1
        ( B ) MAP POSITION: 154-168 (Hermans et al. (1992))

( i x ) FEATURE:
        ( A ) NAME/KEY: misc_feature
        ( B ) LOCATION: 1..10
        ( D ) OTHER INFORMATION: /number=10 /standard_name=
          " Consensus sequence for MPTR sequences"
          / label= NucleicAcid /note= "Actual genomic sequence of
          MPTR-6 154- 168 (1-15) is: CCCGGTGTTGGTGTC (154-168)"

( x i ) SEQUENCE DESCRIPTION: SEQ ID NO:2:

GCCGGTGTTG GTGTC        15

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Mycobacterium ( v i i ) IMMEDIATE SOURCE:
      ( B ) CLONE: IS61

( v i i i ) POSITION IN GENOME:
      ( A ) CHROMOSOME/SEGMENT: Insertion element IS6110
      ( B ) MAP POSITION: 133-114 (Thierry et al., (1990))

( x i ) SEQUENCE DESCRIPTION: SEQ ID NO:3:

GACCGCGGAT CTCTGCGACC                             20

( 2 ) INFORMATION FOR SEQ ID NO:4:

( i ) SEQUENCE CHARACTERISTICS:
          ( A ) LENGTH: 19 base pairs
          ( B ) TYPE: nucleic acid
          ( C ) STRANDEDNESS: single
          ( D ) TOPOLOGY: linear ( i i ) MOLECULE TYPE: DNA (genomic)

( v i ) ORIGINAL SOURCE:
          ( A ) ORGANISM: Mycobacterium ( v i i ) IMMEDIATE SOURCE:
          ( B ) CLONE: IS49

( v i i i ) POSITION IN GENOME:
          ( A ) CHROMOSOME/SEGMENT: Insertion element IS6110
          ( B ) MAP POSITION: 54-72 (Thierry et al., (1990))

( x i ) SEQUENCE DESCRIPTION: SEQ ID NO:4:

CATGTCAGGT GGTTCATCG                              19

( 2 ) INFORMATION FOR SEQ ID NO:5:

( i ) SEQUENCE CHARACTERISTICS:
          ( A ) LENGTH: 22 base pairs
          ( B ) TYPE: nucleic acid
          ( C ) STRANDEDNESS: single
          ( D ) TOPOLOGY: linear ( i i ) MOLECULE TYPE: DNA (genomic)

( v i ) ORIGINAL SOURCE:
          ( A ) ORGANISM: Mycobacterium ( v i i ) IMMEDIATE SOURCE:
          ( B ) CLONE: IS54

( v i i i ) POSITION IN GENOME:
          ( A ) CHROMOSOME/SEGMENT: Insertion element IS6110
          ( B ) MAP POSITION: 1210-1231 (Thierry et al. (1990))

( x i ) SEQUENCE DESCRIPTION: SEQ ID NO:5:

TCGACTGGTT CAACCATCGC CG                          22

( 2 ) INFORMATION FOR SEQ ID NO:6:

( i ) SEQUENCE CHARACTERISTICS:
          ( A ) LENGTH: 15 base pairs
          ( B ) TYPE: nucleic acid
          ( C ) STRANDEDNESS: single
          ( D ) TOPOLOGY: linear ( i i ) MOLECULE TYPE: DNA (genomic)

( v i ) ORIGINAL SOURCE:
          ( A ) ORGANISM: Mycobacterium ( v i i ) IMMEDIATE SOURCE:
          ( B ) CLONE: MPTR-6

( v i i i ) POSITION IN GENOME:

( A ) CHROMOSOME/SEGMENT: MPTR-6
( B ) MAP POSITION: 255-241 (Hermans et al., (1992))

( i x ) FEATURE:
( A ) NAME/KEY: misc_feature
( B ) LOCATION: 3..12
( D ) OTHER INFORMATION: /number=10
/ standard_name= "Consensus sequence for MPTR sequences"/label= NucleicAcid
/ note= "Actual genomic sequence of MPTR-6 at 255-241 is: GGCAGCACTGGGCTC (255-241)"

( x i ) SEQUENCE DESCRIPTION: SEQ ID NO:6:

GGCAACACCG GCCTC  15

( 2 ) INFORMATION FOR SEQ ID NO:7:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Mycobacterium ( v i i ) IMMEDIATE SOURCE:
( B ) CLONE: IS62

( v i i i ) POSITION IN GENOME:
( A ) CHROMOSOME/SEGMENT: Insertion element IS6110
( B ) MAP POSITION: 1237-1256 (Thierry et al. (1990))

( x i ) SEQUENCE DESCRIPTION: SEQ ID NO:7:

ACCAGTACTG CGGCGACGTC  20

( 2 ) INFORMATION FOR SEQ ID NO:8:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Mycobacterium ( v i i ) IMMEDIATE SOURCE:
( B ) CLONE: IS55

( v i i i ) POSITION IN GENOME:
( A ) CHROMOSOME/SEGMENT: Insertion element IS6110
( B ) MAP POSITION: 1330-1312 (Thierry et al. (1990))

( x i ) SEQUENCE DESCRIPTION: SEQ ID NO:8:

TCTGATCTGA GACCTCAGC  19

( 2 ) INFORMATION FOR SEQ ID NO:9:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Mycobaterium tuberculosis
( B ) STRAIN: RFLP type 02-2072 (strain W)

(  v i i  ) IMMEDIATE SOURCE:
            ( B ) CLONE: MDR-7

(  x i  ) SEQUENCE DESCRIPTION: SEQ ID NO:9:

CGCGAGATCT CATCGACAAC C                                                    21

( 2 ) INFORMATION FOR SEQ ID NO:10:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: DNA (genomic)

( v i ) ORIGINAL SOURCE:
            ( A ) ORGANISM: Mycobacterium tuberculosis
            ( B ) STRAIN: RFLP type 02-2072 (strain W)

( v i i ) IMMEDIATE SOURCE:
            ( B ) CLONE: MDR-6

( x i ) SEQUENCE DESCRIPTION: SEQ ID NO:10:

CCAGATATCG GGTGTGTCGA C                                                    21

( 2 ) INFORMATION FOR SEQ ID NO:11:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: DNA (genomic)

( v i ) ORIGINAL SOURCE:
            ( A ) ORGANISM: Mycobacterium ( v i i ) IMMEDIATE SOURCE:
            ( B ) CLONE: IS59

( v i i i ) POSITION IN GENOME:
            ( A ) CHROMOSOME/SEGMENT: Insertion element IS6110

( x i ) SEQUENCE DESCRIPTION: SEQ ID NO:11:

GCGCCAGGCG CAGGTCGATG C                                                    21

( 2 ) INFORMATION FOR SEQ ID NO:12:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: DNA (genomic)

( v i ) ORIGINAL SOURCE:
            ( A ) ORGANISM: Mycobacterium ( v i i ) IMMEDIATE SOURCE:
            ( B ) CLONE: IS60

( v i i i ) POSITION IN GENOME:
            ( A ) CHROMOSOME/SEGMENT: Insertion element IS6110

( x i ) SEQUENCE DESCRIPTION: SEQ ID NO:12:

GATCAGCGAT CGTGGTCCTG C                                                    21

( 2 ) INFORMATION FOR SEQ ID NO:13:

( i ) SEQUENCE CHARACTERISTICS:
    ( A ) LENGTH: 556 base pairs
    ( B ) TYPE: nucleic acid
    ( C ) STRANDEDNESS: double
    ( D ) TOPOLOGY: linear ( i i ) MOLECULE TYPE: DNA (genomic)

( v i ) ORIGINAL SOURCE:
    ( A ) ORGANISM: Mycobacterium ( v i i ) IMMEDIATE SOURCE:
    ( B ) CLONE: NTF-1

( x i ) SEQUENCE DESCRIPTION: SEQ ID NO:13:

```
ACATGGTGAC CGCCGTGAGG CATGGGAAGT GGGTTGTCGA TGAGATCTCG CGCGGAGGTC   60
ACCAGCAGGT ACGCCAAGGC GTATGTGCAG GCTTTGAAGA AGAGCCGGGG CCGGATTTTC  120
GACCAGGTGG TTGACCTGAC GGGCTAGTCA CGTGATAACG CGCGGCGCCG GCTTGTCGCA  180
GCGGCCAAGC TATCGCCGGG GCTGGGCCGC AGTGTTGCCA AGCGGCGGCG CAAACCGCGT  240
TCGCTGAAGT ACTCCTATGA CGCGCTGAAG GTGTTGCAGA GGGTGTGGTC CGCCTCGGGT  300
GGGCAGTGCG GGAAGTATCT TGCCGCCTCG ATGGTGCTGC AGCTTGATGG GTTGGAACGT  360
CACGGTGTGT TGGAGTTTGG GCGTGACCGC TATGGCCCCG AGGTGCGTGA GGAGCTGTTG  420
GCGATGAGTG CGGCCAGCAT CGATCGTTAT CTGAAGACCG CGAAGGCCAA AGACCAGATA  480
TCGGGTGTGT CGACGACGAA ACCCTCACCA CTGCTGCGTA ATTCGATCAA GGTTCGCAGG  540
GCCGGCGATG AGGTCG                                                  556
```

( 2 ) INFORMATION FOR SEQ ID NO:14:

( i ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: YES ( i x ) FEATURE:
        ( A ) NAME/KEY: misc_feature
        ( B ) LOCATION: 1..10
        ( D ) OTHER INFORMATION: /number=10
            / note= "Consensus sequence of 10 bp tandem repeat
            of MPTR (Hermans et al. 1992)"

( x i ) SEQUENCE DESCRIPTION: SEQ ID NO:14:

```
GCCGGTGTTG                                                          10
```

RAPID AMPLIFICATION-BASED SUBTYPING OF MYCOBACTERIUM TUBERCULOSIS

This application is a continuation of application Ser. No. 08/327,005, filed Oct. 19, 1994, which is a continuation of application Ser. No. 08/072,450filed on Jun. 4, 1993, abandoned.

BACKGROUND OF THE INVENTION

1. Field of the Invention

The present invention relates to methods and compounds for rapid identification of clusters of epidemiologically related individual strains of Mycobacterium tuberculosis by a DNA amplification strategy of multiple copy elements of M. tuberculosis. Additionally provided is a method for detecting the presence of M. tuberculosis RFLP-type 021-2072 (or strain W).

2. Background Art

Tuberculosis remains a major source of morbidity and mortality throughout the world and is increasing in the United States today. The resurgence of tuberculosis in the United States is largely related to the human immunodeficiency virus (HIV) epidemic. Because of the reduction in cell-mediated immunity in HIV-infected persons, active disease may develop quickly after exposure to Mycobacterium tuberculosis (Barnes et al., 1991). As the number of hospitalized patients infected with HIV and tuberculosis increases, the risk of nosocomial infection with M. tuberculosis increases not only among patients, but also among health care providers (Pearson et al., 1992).

An important factor in the control of tuberculosis is the ability to identify outbreaks and track the transmission of a particular strain of M. tuberculosis. The standard procedure for distinguishing strains of M. tuberculosis isolates has been phage typing; however, a more sensitive molecular approach has been described recently (Cave et al., 1991). This approach takes advantage of the facts that M. tuberculosis strains carry multiple copies of an insertion sequence, IS6110, and that the precise locations of the IS6110 elements in the M. tuberculosis genome varies significantly from strain to strain, providing a unique DNA fingerprint for each M. tuberculosis strain. The IS6110-restriction fragment length polymorphism (RFLP) technique has been shown to be a reliable and reproducible method for differentiating M. tuberculosis strains (Cave et al., 1991; Otal et al., 1991; van Soolingen et al.), and a recent report utilized this technique to study the epidemiology of multidrug-resistant tuberculosis among hospitalized HIV-infected patients (Edlin et al., 1992). This method allows for the grouping of isolates into fingerprint types.

The IS6110-RFLP procedure requires growth of the organism followed by purification of genomic DNA from the bacteria. The purified DNA is digested with a restriction enzyme which cleaves within the IS6110 sequence. The digested genomic DNA is then electrophoresed on agarose gels, transferred to a membrane, and hybridized with a portion of the IS6110 sequence. This is a time-consuming method that is useful for retrospective epidemiology but has limitations concerning disease management or a rapid response to outbreak situations because of the relatively long time period required to obtain results.

Furthermore, during 1991, the CDC investigated an outbreak of multidrug-resistant tuberculosis (MDR-TB) at a state correctional facility in New York. Eight persons (seven inmates and one correctional facility worker) were identified as having MDR-TB which were resistant to isoniazid, rifampin, ethambutol, streptomycin, kanamycin, ethionamide and rifabutin. All eight patients died within 42 days from the date of collection of their first positive sputum. Restriction fragment length polymorphism (RFLP) analysis for typing Mycobacterium tuberculosis gave identical patterns for seven of the eight strains (eighth strain pending). Epidemiologists state two factors which contributed to this outbreak are 1) length of time required to identify and isolate inmates with active TB from the general prison population and 2) length of time required for identification of M. tuberculosis and the performance of drug susceptibility tests (Greifinger et al.).

This outbreak illustrates the need for a rapid method to detect multidrug-resistant strains of M. tuberculosis including this strain designated M. tuberculosis RFLP-type 021-2072 (or strain W). The strain has increased in prevalence in the New York City area since 1991 due to its multidrug-resistance and is becoming a public health problem. Additionally, there is a strong need for a general method for rapidly, safely and accurately identifying individual strains of M. tuberculosis. In particular, a method that eliminates the need for culturing the slow-growing, highly infective virulent M. tuberculosis cells would be much more useful and desireable than any presently-existing method.

SUMMARY OF THE INVENTION

The present invention relates to methods of detecting or distinguishing the DNA of an individual strain of Mycobacterium tuberculosis utilizing the polymerase chain reaction (PCR). Reproducible, unique patterns can be produced allowing the identification of unknown M. tuberculosis DNA by performing this reaction and comparing the pattern produced to the known reproducible, unique patterns.

The invention further relates to a kit useful to detect or distinguish the DNA of an individual strain of M. tuberculosis in a sample, comprising specific primers for use in PCR.

The instant invention also relates to a method of determining the presence of a multidrug-resistant M. tuberculosis by detecting the presence of a specific arrangement of genomic DNA. Such detection can be done using PCR or a ligase chain reaction (LCR).

Finally, the present invention relates to nucleic acid sequences useful in detecting multidrug-resistant M. tuberculosis.

Accordingly, it is an object of the instant invention to provide methods of detecting or distinguishing the DNA in a sample to identify the individual strain present. A further object is to provide a kit containing specific primers useful for such detection and identification.

It is an additional object to provide methods and primers to detect the presence of multidrug-resistant strains of M. tuberculosis in a sample to allow rapid diagnosis and proper treatment of infected individuals.

DESCRIPTION OF THE DETAILED INVENTION

The present invention may be understood more readily by reference to the following detailed description of specific embodiments and the Examples and Figures included therein.

The invention involves the use of nucleic acid amplification such as polymerase chain reaction (PCR) (Mullis & Faloona, 1987) and a hybridization procedure to measure the variability in the distances between IS6110 elements and a major polymorphic tandem repeat (MPTR) sequence of *M. tuberculosis* (Hermans et al., 1992; Shinnick, 1987). Other amplification methods now known, for example, ligase chain reaction, or developed later can easily be adapted, given the teachings herein, to perform the methods of the claimed invention.

Figure 1:
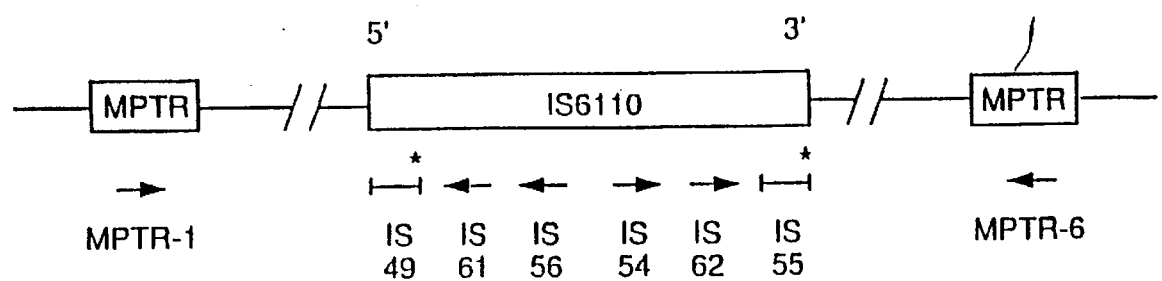
FIG. 1 shows schematic representation of IS6110 and MPTR sequences and the location of oligonucleotides used in PCR and Southern blotting. * denotes the ECL fluorescein labelled oligonucleotide used as a probe in the Southern blot.

The method of the present invention, termed "ampliprinting," involves the following general strategy. The relative positions of the oligonucleotides used to assess the distances between IS6110 elements and MPTR elements are shown in FIG. 1. The first round of amplification uses a primer specific for either the left or right end of IS6110 and a primer specific for the MPTR. Both primers are oriented to amplify sequences flanking the repeated elements. A second round of amplification using the same MPTR primer and a second, nested IS6110 primer is performed to increase the specificity of the reaction for the IS6110 element. Finally, the reaction products can be visualized by electrophoresis blotting and hybridization to a third IS6110-specific detectably labeled nucleic acid probe. The last step identifies the IS6110-containing amplicons among the background amplifications due to non-specific priming and to amplicons produced within the MPTR regions.

Therefore, this invention provides a method of creating a reproducible, unique pattern for identifying in a sample the DNA of an individual strain of *Mycobacterium tuberculosis* to detect or distinguish between *Mycobacterium tuberculosis* strains comprising performing a polymerase chain reaction utilizing primer sets that amplify between an IS6110 insertion element and a major polymorphic tandem repeat element to form a unique polymerase chain reaction product; and visualizing the polymerase chain reaction product to reveal the unique pattern that detects or distinguishes the *Mycobacterium tuberculosis* strain.

A "unique pattern" is a unique DNA banding arrangement when the sizes of amplification fragment are visualized, as by electrophoresis through a gel, whether the pattern is revealed through, for example, ethidium bromide staining and UV light, blotting the gel and hybridizing with a detectably labeled probe which is then detected, or by any other method. The pattern is "unique" when it is specific to a particular IS6110-RFLP fingerprint type, as described in Cave et al. 1991, and exemplified by the groupings in Table 1. As used herein, a "strain" of Mycobacterium is interchangeable with a "fingerprint type." The visualizing step can be accomplished by contacting the polymerase chain reaction product with a detectably labeled nucleic acid probe which hybridizes to a portion of the IS6110 insertion element that is 3' to the first primer, and visualizing the size of the polymerase chain reaction product.

The performing step can be accomplished by performing a first polymerase chain reaction with the sample utilizing a first primer set comprising a first oligonucleotide primer which selectively hybridizes to a first portion of an IS6110 insertion element and a second oligonucleotide primer which selectively hybridizes to a portion of a major polymorphic tandem repeat element of *Mycobacterium tuberculosis* to form a first polymerase chain reaction product, and performing a second polymerase chain reaction with the first polymerase chain reaction product utilizing a second primer set comprising the second oligonucleotide primer and a third oligonucleotide primer which selectively hybridizes to a second portion of the IS6110 insertion element which is 3' to the first primer to form a second polymerase chain reaction product. This product can be visualized by contacting the second polymerase chain reaction product with a delectably labeled nucleic acid probe which selectively hybridizes to a portion of the IS6110 insertion element that is 3' to the third primer, and visualizing the size of the second polymerase chain reaction product to which the labeled nucleic acid probe has selectively hybridized.

Alternatively, after the first round of amplification, the first polymerase chain reaction product can be subjected to selective hybridization by contacting it with an IS6110-specific nucleic acid probe which selectively hybridizes to a portion of the IS6110 insertion element that is 3' to the second primer and that is bound to a solid support. Unhybridized first PCR product is then removed, and hybridized PCR product released and subjected to the second round of amplification as described above. However, with this alternative method, the last step (that of hybridization with a detectably labeled nucleic acid probe to visualize the size of the second PCR product) can be omitted, as product specificity for IS6110-containing amplicons among background amplifications was provided by hybridization with the substrate-bound probe. The product of the second round of amplification can be visualized thereafter by electrophoresis with ethidium bromide and then applying UV light.

The "major polymorphic tandem repeat element" of *M. tuberculosis*, or MPTR, is the repeat element described in Shinnick and in Hermans et al. The MPTR sequence is composed of tandem repeats of a 10 basepair consensus sequence separated by 5 bp highly heterogeneous spacers. The consensus sequence of the 10 bp tandem repeat is (5') GCCGGTGTTG, listed in SEQ ID NO: 14, which has homology to the repetitive extragenic palindromic (REP) sequences of *Escherichia coli* (Hermans et at., 1992). These tandem repeats are found in the *M. tuberculosis* genome in as many as 80 different regions. Importantly, their distribution in the *M. tuberculosis* genome appears to be stable, in contrast to the variability in IS6110 location. Thus; by using IS6110 and MPTR primers in a nested amplification procedure followed by hybridization with an IS6110-specific oligonucleotide, a pattern of amplification products is generated that clusters strains of *M. tuberculosis* into groups matching those formed using the IS6110-RFLP technique.

As used herein, a nucleotide sequence that "selectively" hybridizes is one that specifically hybridizes to its target nucleic acid based upon sufficient complementarity of the two sequences, rather than random, non-specific hybridization. In other words, the sequences utilized for hybridization are unique to the sequences in the sample such that they can be detected.

For example, an oligonucleotide primer which "selectively hybridizes to a first portion of a major polymorphic tandem repeat element" is meant to include any sequence complementary to a portion of an MPTR that, when used as one of the primers in a PCR reaction as described herein, would produce an identifiable product that is not too complex, i.e., a distinguishable number of distinct bands rather than a ladder or a smear, when electrophoresed through a gel. Primers can be tested utilizing the methods described herein. Preferred primers include 15 to 20 nucleotides, with the 10 nucleotides that are complementary to the consensus sequence centered between 5 to 10 nucleotides that are complementary to the heterogenous spacers. The most preferred primers have (in the 5' to 3' direction) two nucleotides of spacer followed by 10 nucleotides of consensus followed by 3 nucleotides of spacer. Optimal spacer sequences are those that, according to the sequences of Shinnick and of Hermans et al., only occur once within the MPTR. Examples of preferred primers having unique spacer sequences are seen in SEQ ID NOS: 2 and 6. Additionally, rather than using the consensus sequence itself for the interior 10 nucleotides, if desired, one could utilize the actual sequences of any of these regions.

Primers that "selectively hybridize to a portion of an IS6110 insertion element" can be chosen according to the published sequence of this element (Thierry et al.) and according to established general guidelines for choosing primer sequences, for example, Innis et al. Examples of such primers are listed as SEQ ID NOS: 1, 3, 4, 5, 7, 8, 11 and 12 (see also FIG. 1).

As used in the claims, "a" can mean one or more.

Visualizing the size of any PCR product can be accomplished by, for example, electrophoresing the product alongside marker nucleic acids of known size through a gel, for instance, an agarose or a polyacrylamide gel, by standard techniques known in the art (see Sambrook et al.). When a compound such as ethidium bromide is added to the product prior to electrophoresis, the DNA can be directly viewed in the gel with UV light. Additionally, one can blot and fix the DNA from the gel onto a filter and hybridize to it a detectably labeled nucleic acid probe. The detectable label is any now known, or developed in the future, label that allows one to visualize the hybridized probe and can comprise, for example, fluorescein, digoxigenin, or a radioactive isotope, with fluorescein being the presently preferred label. The means for labeling the nucleic acid probe are known to those skilled in the art (see, e.g., Sambrook et al.) "A polymerase chain reaction product" means the product of a PCR reaction, and can include one or, more typically, several fragments which, if of different lengths, appear on a gel as several bands.

Furthermore, if one chooses to hybridize the first polymerase chain reaction product with a probe that is bound to a solid support, there is no need to blot the PCR product from the second PCR reaction and hybridize it with a delectably labeled probe. A "solid support" can include, for example, a laboratory plate or dish to which the probe is covalently linked, as is known in the art, or a metallic bead to which the probe is bound and which can be removed from unhybridized first PCR product by applying a magnetic field. A probe can be bound to a metallic bead, for example, by using a streptavidin-coated bead and a biotin label on the probe, which, when the streptavidin contacts the biotin on the probe, will link the probe to the bead via the biotin-streptavidin link (Dynal, Inc., *Technical Handook: Dynabeads Biomagnetic Separation System*, First Ed. (1992) Dynal, Inc., 475 Northern Blvd., Great Neck, N.Y. 11021).

Once unhybridized first reaction product is removed, as by applying a magnetic field, if metallic beads are used, or by washing the plate, if probe linked to a plate is used, the hybridized first reaction product is released from the bound probe by applying denaturing conditions to separate the product from the bound probe. This IS6110-specific fraction of the first reaction product can now be used in the second round of PCR, as described herein. Once the second round is complete, the second PCR products can be electrophoresed through a gel with ethidium bromide and directly visualized with UV light. The need for blotting and hybridizing this gel with a detectably labeled IS6110 probe is eliminated, as IS6110 specificity was applied to the product after the first round of PCR.

A primer that "consists essentially of" the nucleic acid set forth in a sequence listing includes not only a primer having a sequence identical to those in the sequence listing but also any addition, substitution or deletion which still hybridizes to the homologous region of the genomic DNA to form a unique PCR product. Thus, preferred primer and probe sets for the above embodiment of the invention include sequences consisting essentially of: (1) first primer: SEQ ID NO: 1; second primer: SEQ ID NO: 2; third primer: SEQ ID NO: 3; probe: SEQ ID NO: 4; (2) first primer: SEQ ID NO: 5; second primer: SEQ ID NO: 6; third primer: SEQ ID NO: 7; probe: SEQ ID NO: 8.

Additionally provided is a kit comprising a first primer which is capable of selectively hybridizing to an IS6110 insertion element of *Mycobacterium tuberculosis* and a second primer which is capable of selectively hybridizing to the major polymorphic tandem repeat element of *Mycobacterium tuberculosis* to amplify the region between the primers. The kit can further comprise a third primer capable of selectively hybridizing to a portion of the IS6110 insertion element which is 3' of the first primer. Such primers that are "capable of selectively hybridizing" with a specified region of DNA include, for example, primers consisting essentially of the nucleic acids set forth in (1) SEQ ID NO. 1, 3-5, 7, 8, 11 and 12 for primers capable of selectively hybridizing to an IS6110 insertion element, and (2) SEQ ID NO. 2 and 6 for primers capable of selectively hybridizing to the major polymorphic tandem repeat element (MPTR). Preferred first, second and third primers are listed above. The primers can also be any addition, substitution or deletion of these sequences which is still capable of hybridizing to the homologous region of the genomic DNA, i.e., which is sufficiently complementary to the sequence to allow it to hybridize to the sequence when placed in conditions suitable for hybridization (see Sambrook et al.). Other primers capable of selectively hybridizing to IS6110 and MPTR can be developed as discussed previously by analyzing the published sequences of IS6110 and MPTR according to general guidelines (e.g., Innis et al.).

Also provided in the kit is a nucleic acid probe capable of detecting the region between the primers. Such probe can be delectably labeled as described previously or can be bound to a substrate as described previously. Examples of nucleic acid sequences useful as a detectable probe include SEQ ID NO. 4 and 8; however, any addition, substitution or deletion of these sequences which can still hybridize to the region between the primers or any other sequences that hybridize to the region between the primers as well as other primers can be utilized. Preferred probes hybridize to IS6110 sequences located between the primers, since IS6110 has only been found in members of the *M. tuberculosis* complex and since such probes would not hybridize to products produced solely with the MPTR primer; therefore, by use. Of an IS6110 probe, the overall pattern is simplified and the detection of strain-to-strain variation is enhanced. Some preferred probes are listed above along with the preferred primer set to be used with each one. Depending upon the specific method utilized, the probe can be chosen to be capable of hybridizing to a region between the first and second primer or the second and third primer (see FIG. 1). The probe can be utilized either between the first and second rounds of PCR or after the second round of PCR, as described previously.

As used in the claims, a "sample" in which M. tuberculosis is detected can include any material which can contain M. tuberculosis DNA such that PCR can be performed with the DNA. Examples include crude lysates of cell cultures and patient specimens, such as sputum and bronchial washings.

Additionally provided is a method of determining the presence specifically of multidrug-resistant strains of M. tuberculosis in a sample, comprising a method of determining the presence of a multidrug-resistant Mycobacterium tuberculosis in a sample, comprising detecting the presence of an approximately 556 nucleotide DNA fragment between a direct tandem repeat of insertion element IS6110, the presence of the fragment indicating the presence of a multidrug-resistant Mycobacterium tuberculosis in the sample. These multidrug-resistant strains are those which contain an approximately 556 nucleotide DNA fragment (NTF-1, listed in SEQ ID NO: 13) between a direct tandem repeat of insertion element IS6110. These strains are resistant to at least the following five drugs: isoniazid, rifampin, ethambutol, streptomycin and rifabutin. Additionally, the strains may have resistance to one or more other drugs including kanamycin and ethionamide. Examples of these strains include the following strains maintained at the Centers for Disease Control, Mycobacteriology Laboratory, Division of Bacterial and Mycotic Diseases, Atlanta, Ga.: 91-2870, 91-3006, 91-3378 and 91-2967. RFLP type 021-2072 (strain W) is resistant to all seven drugs listed above (Greifinger et al.). This strain exhibits a known RFLP pattern when its genomic DNA is cut with, for instance, PvuII restriction endonuclease. Other multidrug-resistant strains, as used herein, have RFLP patterns very similar or identical to that of RFLP type 021-2072, depending upon the restriction enzyme used, since different strains may have polymorphisms that alter a restriction endonuclease site. All strains included in this aspect of the invention, however, have the configuration of FIG. 2, i.e., the NTF-1 fragment located precisely between a direct tandem repeat of insertion element IS6110.

Polymerase chain reaction analysis of the flanking regions of IS6110 with primers specific for sequences at the 5' and 3' ends of IS6110 revealed this arrangement of a direct tandem repeat of IS6110 with an approximately 556 basepair intervening sequence in the multidrug-resistant *M. tuberculosis* RFLP-type 021-2072 (strain W), as well as other multidrug-resistant strains such as those named above (see FIG. 2). The location and orientation of this 556 bp fragment, designated NTF-1, is specific for the multidrug-resistant strains of *M. tuberculosis* of this invention. The NTF-1 sequence itself is found in all *M. tuberculosis* tested. This orientation of the IS6110 direct tandem repeat and the NTF-1 spacer is therefore the target of a multiplex PCR method that specifically determines the presence of these multidrug-resistant strains of *M. tuberculosis* including RFLP-type 021-2072.

The presence of multidrug-resistant *M. tuberculosis* in a sample can be determined by detecting the presence of this 556 nucleotide NTF-1 fragment, listed as SEQ ID NO. 13, between direct tandem repeats of insertion element IS6110, the presence of the fragment indicating the presence of a multidrug resistant *M. tuberculosis* in the sample. A preferred method of detecting this DNA arrangement is to detect the presence of the two unique junctions of NTF-1, at either end, with IS6110 (see FIG. 3) (the "first junction" and the "second junction"). The "junction" is the point where the last nucleotide of IS6110 or NTF-1 is linked to the first nucleotide of NTF-1 or IS6110, respectively. Each junction can be detected by amplification methods such as PCR wherein a primer that has homology, and thus will hybridize to a region on each side of each junction, and is oriented such that the PCR product from each primer is synthesized toward the other, i.e., toward the junction, is utilized to generate a product of predictable size based upon the map of the region and the particular primers chosen. Primers for PCR reactions utilized to detect multidrug resistant strains in this invention should be chosen particularly so that the predicted size of the individual product of any one set of primers will be different from the product of any other set, in order to be able to distinguish the individual product fragments on the gel. The products of the amplification can be electrophoresed and visualized with, for example, ethidium bromide, under UV light. The presence of both predicted PCR products indicates the presence of this genomic DNA arrangement.

Specifically, one can perform the detection of "multidrug-resistant strain of *M. tuberculosis* by (a) performing a polymerase chain reaction utilizing a first and second set of oligonucleotide primers, the first set comprising a first primer which selectively hybridizes to a region of IS6110 such that a polymerase chain reaction product synthesized from the first primer is synthesized toward the first junction, and a second primer which selectively hybridizes to a region of the fragment such that a polymerase chain reaction product synthesized from the second primer is synthesized toward the first junction and the second set comprising a third primer which selectively hybridizes to a region of the fragment such that a polymerase chain reaction product synthesized from the third primer is synthesized toward the second junction and a fourth primer which selectively hybridizes to a region of IS6110 such that a polymerase chain reaction product synthesized from the fourth primer is synthesized toward the second junction; (b) determining the size of the polymerase chain reaction product; and (c) associating the polymerase chain reaction product with the polymerase chain reaction product of a *Mycobacterium tuberculosis* having the approximately 556 bp nucleotide DNA fragment between the direct tandem repeat of IS6110.

Additionally, once this reaction is performed with identical primers on a sample known to contain only, for example, *M. tuberculosis* RFLP-type 021-2072 DNA, the pattern thus generated upon visualizing the PCR products can be used to compare experimental samples. A match, or "an association," between the pattern generated by the known sample and the experimental sample indicates that the sample contains DNA from a multidrug-resistant strain of *M. tuberculosis*, as defined herein.

Particularly useful, in addition to the reactions using primers surrounding and amplifying the two junctions of NTF-1 with the IS6110 tandem repeat, is an additional reaction to serve as a positive control test to indicate the production of an *M. tuberculosis* PCR product. A preferred positive control test involves utilizing a third set of oligonucleotide primers comprising a fifth primer which selectively hybridizes to a region of IS6110 and a sixth primer which selectively hybridizes to a second region of 186110, such that a polymerase chain reaction product synthesized from the fifth primer/s synthesized toward the sixth primer and a polymerase chain reaction product synthesized from the sixth primer is synthesized toward the fifth primer, wherein the production by polymerase chain reaction of a product of the fifth primer and the sixth primer indicates the presence of *Mycobacterium tuberculosis*. Amplification of an IS6110 fragment exemplifies an effective positive control, as IS6110 is found only in members of the *M. tuberculosis* complex, but other controls can be used.

Specific primers useful for detecting the first junction include IS 62 (SEQ ID NO. 7) and MDR-7 (SEQ ID NO. 9), which produce a 175 bp PCR product; primers useful for detecting the second junction include MDR-6 (SEQ ID NO. 10) and IS 61 (SEQ ID NO. 3), which produce a 223 bp PCR product; and primers useful as a positive PCR control include IS 59 (SEQ ID NO. 11) and IS 60 (SEQ ID NO. 12), which produce a 523 bp PCR product. However, many other suitable primers may be determined by assessing the nucleotide sequence of these regions and applying the general guidelines for selecting primer sequences (see e.g., Innis et al.). The reaction products from any chosen set of primers can be readily predicted from the map and nucleotide sequence of the region.

The detection of the genomic DNA arrangement of NTF-1 between a tandem repeat of IS6110 of multidrug-resistance strains as described herein can also be performed using a ligase chain reaction (LCR) (Iovannisci et al. (1993), Wu et al. (1989)) utilizing a first and second set of oligonucleotide primers, the first set comprising a first primer which selectively hybridizes to one strand of IS6110 immediately 5' to the first junction and a second primer which selectively hybridizes to the same strand of the fragment immediately 3' to the first junction such that a ligase chain reaction product can be formed with the two primers, and the second set comprising a third primer which selectively hybridizes to one strand of the fragment immediately 5' to the second junction and a fourth primer which selectively hybridizes to the same strand of IS6110 immediately 3' to the second junction such that a ligase chain reaction product can be formed with the two primers; then determining the size of the ligase chain reaction product, and associating the size of the ligase chain reaction product of each primer set with the additive size of the two primers comprising the primer set to indicate the presence of the first and second junctions.

Essentially, this reaction, known to those of skill in the art, involves the use of, for each region to be detected, two primers that hybridize to the same strand of the target DNA, either abutting each other or with one or two nucleotides between the two primer sequences (i.e., "immediately 5'" or "immediately 3'" to the junction). The ligase reaction is performed, and the products are electrophoresed through a gel that can detect very small fragments, such as a polyacrylamide gel. A positive result is one in which a product equal in size to the sum of the two primers is produced, as this indicates the presence of all of the target DNA region. It is preferable that three reactions be run in three separate tubes, targeted at detecting (1) the first junction, (2) the second junction and (3) an internal IS6110 as a positive LCR control. If one wants to electrophorese all LCR products together through the gel, primers can be carefully chosen such that their individual sizes can be distinguished from the predicted size of any LCR products, or distinct fluorescent tags can be used to label each primer, such that each primer and each LCR product can be distinguished when electrophoresed and, if desired, analyzed by a Genescanner (Iovannisci et al. (1993)). Alternatively, the product of each reaction can be electrophoresed separately. Primers are preferably exactly homologous to the target region (as can be chosen from the published IS6110 sequence and the NTF-1 sequence provided herein as SEQ. ID NO: 13) and of a size between approximately 20–40 nucleotides.

As used herein, "a unique portion" of a nucleic acid includes any portion having a nucleotide sequence that substantially does not occur in nucleic acids that would occur in the test sample. As examples, SEQ ID NO. 9 and SEQ ID NO. 10 are unique portions of the nucleic acid having the sequence set forth in SEQ ID NO. 13.

The present invention is more particularly described in the following examples which are intended as illustrative only since numerous modifications and variations therein will be apparent to those skilled in the art.

EXAMPLES

Bacterial strains and preparation of DNA.

The strains used in this study are listed in Table 1. DNA was prepared from *M. tuberculosis* isolates using the CTAB (cetyltrimethylammonium bromide) method as previously described (Wilson 1990). Crude lysates of the non-*M. tuberculosis* strains listed in Table 1 were prepared by glass bead lysis as previously described (Plikaytis et al., 1992).

TABLE 1

| Species | Strain or Isolate Number | Fingerprint type* |
|---|---|---|
| M. tuberculosis | 91-8358, 91-8359, 91-8360 | 011-8114 |
| M. tuberculosis | 91-8361, 91-2627, 91-2742, 91-2743, 91-2744, 91-2745, 91-2746, 92-8081, 92-8082, 92-8083, 92-8088, 92-8089, 92-8090, 92-8091, 92-8092, 92-8093, 92-8095 | 021-2072 |
| M. tuberculosis | 91-8271, 91-8272, 91-8273 | 023-8271 |
| M. tuberculosis | 91-8275, 91-8276 | 024-8275 |
| M. tuberculosis | 92-8078, 92-8079 | 036-8078 |
| M. tuberculosis | 92-8084, 92-8085, 92-8086 | 036-8084 |
| M. tuberculosis | 91-3048 | 028-3048 |
| M. tuberculosis | 91-3054 | 028-3054 |
| M. tuberculosis | 91-8309 | 031-8309 |
| M. tuberculosis | 91-8310 | 031-8310 |
| M. tuberculosis | 91-8311 | 031-8311 |
| M. tuberculosis | 91-8312 | 031-8312 |
| M. tuberculosis | 91-8313 | 031-8313 |
| M. tuberculosis | 91-8270 | 023-8270 |
| M. tuberculosis | 91-8277 | 024-8277 |
| M. tuberculosis | H37Rv | H37Rv |
| M. bovis | TMC 401, TMC 410 | |
| M. bovis, BCG | TMC 1024 | |
| M. africanum | TMC 5122 | |
| M. avium | TMC 1461 | |
| M. chelonae | TMC 1524 | |
| M. fortuitum | TMC 1530 | |
| M. gastri | ATCC 25157 | |
| M. gordonae | TMC 1325 | |
| M. intracellulare | TMC 1469 | |
| M. kansasii | ATCC 12478 | |
| M. scrofulaceum | TMC 1312 | |
| M. smegmatis | TMC 1533 | |
| M. szulgai | 91-698 | |

*The IS6110-RFLP fingerprint type consists of outbreak or study number followed by the isolate number. All subsequent isolates having that identical fingerprint pattern are given the same type designation as the initial isolate having that pattern.

Preparation of lysates from sputum specimens.

Smear-positive sputum samples were obtained from the Arkansas State Health Department laboratory. The specimens were liquified and decontaminated using the standard n-acetylcysteine-NaOH protocol (Kent and Kubica, 1985), and the sediments remaining after microscopy and inoculation on solid media were stored at −20° C. until they were processed for PCR. The sediment was centrifuged at 16,000 G for 5 min and the supernatant was discarded. The pellet was resuspended in 200 ul of 10 mM Tris hydrochloride (pH 8.0)-1 mM EDTA-10 mM NaCl and mixed with 200 ul of siliconized 0.1-mm-diameter glass beads and 100 ul of chloroform. The mixture was homogenized for 2 min at room temperature in a Mickle apparatus (Brinkman Instruments, Westbury, N.Y.) to disrupt the cells. The homogenized suspension was centrifuged at 16,000 G for 5 min, and the aqueous supernatant was transferred to a fresh tube and boiled for 10 min.

Oligonucleotide primers.

Primers corresponding to portions of the M. tuberculosis IS6110 and MPTR sequences were synthesized on a DNA synthesizer (model 381A; Applied Biosystems, Foster City, Calif.) at the Biotechnology Core Facility, Centers for Disease Control. The sequences and locations of these primers are listed in SEQ IDs 1–12, and the relative positions within the IS6110 sequence are depicted in FIG. 1. The MPTR-primer sequences were determined by combining the consensus sequence for the 10 bp repeat with five flanking bases, which were selected by comparing the reported sequences (Hermans, et al., 1992; Shinnick, 1987) and identifying 5 bp spacer sequences which appeared only once in each reported sequence.

Gene amplification.

The amplification reaction contained 10 ul of template DNA and 90 ul of a reaction mix (200 uM [each] deoxynucleotide triphosphates, 1.0 uM [each]primers, 2.5 U of Taq polymerase, 10 mM Tris hydrochloride [pH 8.3], 50 mM KCl, 1.5 mM $MgCl_2$, 0.01% gelatin) as recommended by the Taq polymerase manufacturer (Perkin-Elmer Cetus, Norwalk, Conn.). The first round of amplification with an IS6110 primer and an MPTR primer consisted of 25–30 cycles in a programmable thermal cycler (Perkin-Elmer Cetus) with a three step cycle of denaturation for 1.5 min at 94° C., annealing for 1.75 min at 45° C., and extension for 2.5 min at 72° C. The second round of amplification was carried out for 15–25 cycles after transferring 10% of the first round amplification mixture to a fresh tube containing reaction mixture with a nested IS6110 primer and the same MPTR primer used in the first round. The second round of amplification used a three step cycle similar to that used in the first round, except that the annealing temperature was 60° C.

Hybridization.

Fifteen microliters of the second round amplification mixture were electrophoresed on a 1.5% agarose gel, and the reaction products were visualized by ethidium bromide fluorescence. The DNA was then denatured, neutralized, and transferred by capillary blotting to Hybond-N+ membrane (Amersham Corporation, Arlington Heights, Ill.) as recommended by the manufacturer of the membrane. DNA was bound to the membrane using a stratalinker UV crosslinker (Stratagene, La Jolla, Calif.). An IS6110 (IS49 or IS55) or MPTR (MPTR-6) specific oligonucleotide was labeled using the ECL 3'-oligolabeling and detection system (Amersham Corp.). The membrane was hybridized according to the manufacturer's recommendations at 42° C. for 3 h and washed stringently at 42° C. in 3 mM sodium citrate, 30 mM sodium chloride, and 0.1% sodium dodecyl sulfate. After development with the ECL detection solutions, the signals were detected using X-OMAT AR autoradiography film (Eastman Kodak Co., Rochester, N.Y.).

Evaluation of primers for M. tuberculosis amplified fingerprinting (amplityping).

The sites of insertion of IS6110 within the M. tuberculosis genome have been shown to be variable yet stable enough to be a meaningful marker to type M. tuberculosis isolates (Cave et al., 1991; Oral et al., 1991). To develop a PCR-based procedure to assess this variability and thereby rapidly differentiate M. tuberculosis strains, we paired oligonucleotide primers from the IS6110 sequence with a primer from a second repeated sequence, MPTR. The MPTR sequence is an ideal sequence to pair with IS6110 because it is predicted to appear in 80 different sites in the *M. tuberculosis* genome (Hermans et al., 1992), and the distribution of the MPTR sequences within the genome has been shown to be conserved among *M. tuberculosis* isolates (Hermans et al., 1992), making the locations of IS6110 in the genome the variable factor. The MPTR consensus sequence shares homology with the REP sequence of *Escherichia coil* (Hermans et al., 1992). A recent report stated that there are 563 copies of the REP sequence in 295 clusters in the *E. coli* genome (Dimri et al., 1992). The utility of the REP sequence in PCR-based fingerprinting was shown by Versalovic et al. (1991) when REP sequences were used to produce fingerprints from various bacterial genomes.

The MPTR primer sequences were selected by comparing the sequences reported by Hermans et al. (1992) and Shinnick (1987) and using the core consensus sequence plus a set of additional bases that appeared only once in each reported sequence of repeats. Two sets of IS6110-specific primers, one at the left (IS56, IS61, IS49) and one at the right (IS54, IS62, IS55) end were evaluated. Each set contained two nested primers for amplification and a third for use as a hybridization probe (FIG. 1). Initially six MPTR primers were tested with each of the two sets of IS6110 primers. MPTR-1 was found to produce the most informative patterns when paired with the IS6110 left set of primers, and MPTR-6 was found to be best for use with the IS6110 right set (data not shown). These primers and the IS6110 primers were then used individually and in combination with each other to characterize further the amplification patterns produced from *M. tuberculosis*. That is, strain 91-8361 DNA was amplified using IS56 alone, MPTR-1 alone, IS56 +MPTR-1 (first round), and IS56+MPTR-1 followed by IS61+MPTR-1 (second round), or using IS54 alone, MPTR-6 alone, IS54+MPTR-6, and IS54+MPTR-6 followed by IS62+MPTR-6. DNA fragments ranging in size from approximately 250 to 2200 bp were amplified by each primer individually or by each combination of primers tested. To enhance the signal from the IS6110-containing amplicons, the samples were hybridized with an IS6110-specific oligonucleotide probe. The hybridization step eliminated the signals from the products amplified due to mispriming or due solely to the MPTR primer and produced a discrete pattern of 9 to 11 IS6110-containing amplicons.

The primer MPTR-6, which when paired with IS54 gave the most reproducible and distinctive patterns, is composed of the consensus sequence flanked by two bases on the 5'-end and a unique set of three bases on the 3'-end. A 45° C. annealing temperature was used in the first round of amplification to allow for potential mismatches in the slightly heterogeneous MPTR consensus sequence. The second round, which is not a true nested amplification since the same primer is used for the MPTR sequence, employs a more stringent annealing temperature of 60° C. The use of two IS6110-specific primers and the increased annealing temperature improves the efficiency of amplification of IS6110-containing sequences. The use of an IS6110-specific oligonucleotide probe for hybridization identifies those fragments containing the IS6110 sequence and eliminates those produced from priming solely with the MPTR-6 primer. This simplifies the overall pattern by removing conserved MPTR-derived amplicons and enhances the detection of strain-to-strain variation.

Comparison of 5'-end and 3'-end primer sets.

To determine which set of primers was the most useful or if data from both sets would be necessary to distinguish different strains of *M. tuberculosis*, 16 strains were amplified using primer sets IS56+MPTR-1 (5'-end) and IS54+MPTR-6 (3'-end) in the first round followed by a second round of amplification with IS61+MPTR-1 (5'-end) and IS62 +MPTR-6 (3'-end) and then were hybridized with the corresponding probe. The 16 strains analyzed represent six distinct IS6110-RFLP types (JTC, unpublished data). Each set of primers generated a distinctive pattern of IS6110-containing amplicons for each of the four IS6110-RFLP types. The 3'-end primer set was chosen for further study because it appeared to give a slightly more reproducible pattern.

Reproducibility of amplitypes generated by the 3'-end primer set. *M. tuberculosis* isolates from serial specimens from five patients representing three IS6110-RFLP types were evaluated using the 3'-end primer set and probe. The pattern of ethidium bromide stained bands appeared to be unique to each IS6110-RFLP type, and these differences were enhanced by hybridization with the IS6110-specific oligonucleotide. Importantly, each isolate from a serial specimen set produced the same pattern of fragments upon amplification and hybridization and each set displayed a characteristic amplitype.

Sensitivity and specificity of the 3'-end primer set.

Purified DNA from *M. tuberculosis* H37Rv was titrated to determine the detection limit of the method using 30 cycles of amplification in the first round of amplification and 15 cycles in the second round of amplification. The pattern of IS6110-containing amplicons was maintained to 100 pg of DNA, which is equivalent to approximately $2\times10^4$ organisms (dam not shown). At smaller amounts of DNA, the major PCR products were still amplified; however, several of the minor amplification products were not. This reduced the amount of information in the patterns, which, in turn, may lessen the ability of the method to differentiate strains.

The specificity of the method was evaluated by amplifying crude lysates of *M. africanum, M. avium, M. bovis, M. bovis* BCG, *M. chelonae, M. fortuitum, M. gastri, M. gordonae, M. intracellulare, M. kansasii, M. scrofulaceum, M. smegmatis*, and *M. szulgai*. Various numbers of ethidium-bromide stained fragments were amplified from each species. However, only the *M. africanum* sample contained amplicons that hybridized with the IS6110-specific IS55 oligonucleotide (data not shown).

Since IS6110 is found only in members of the *M. tuberculosis* complex (*M. tuberculosis, M. bovis, M. africanum, M. microti*), the amplification plus hybridization procedure should be specific for the *M. tuberculosis* complex. Amplification of *M. africanum, M. avium, M. bovis, M. bovis* BCG, *M. chelonae, M. fortuitum, M. gastri, M. gordonae, M. intracellulare, M. kansasii, M. scrofulaceum, M. smegmatis*, and *M. szulgai* using the 3'-end set of primers did produce various numbers of ethidium bromide stained fragments for each strain, but only the *M. africanum* lysate showed hybridization to the IS6110-specific oligonucleotide. The negative hybridization results with *M. bovis* and *M. bovis* BCG are not surprising, however, since there are only 1 to 3 copies of the IS6110 sequence in the *M. bovis* genome. Likewise, the positive hybridization results with *M. africanum* are expected since this strain contains 6 to 9 copies of the IS6110 sequence (Plikaytis et at., 1991).

Many fragments in the amplified samples from each of the Mycobacterium species tested hybridized to MPTR-6 (data not shown). This suggests that sequences homologous to the MPTR consensus sequence are present in the genome of each of these species. However, these amplification results do not distinguish clusters of tandem repeats from fortuitous positioning of individual sequences homologous to the MPTR primer. The latter may be important because a Southern hybridization analysis of genomic DNA suggested that clusters of homologous tandem repeats were found in only *M. tuberculosis* complex species, *M. gastri, M. gordonae, M. kansasii*, and *M. szulgai* (Hermans et al., 1992).

Clinical isolates and sputum specimens.

Type strain H37Rv and 39 *M. tuberculosis* clinical isolates from seven tuberculosis outbreak investigations representing 16 IS6110-RFLP types were analyzed with the 3'-end primer set. Each of the 16 IS6110-RFLP types produced a unique set of IS6110-containing amplicons. Furthermore, strains that had identical IS6110-RFLP patterns also had identical IS6110-amplicon patterns.

Six smear-positive (3 to 4+) sputum specimens from three tuberculosis patients were processed as described above, and the crude lysates were amplified for 30 cycles in the first round and 25 cycles in the second round using the 3'-end primers. Identical hybridization patterns were observed for each of the three replicate specimens from one patient, while the amplitypes generated from each patient's specimens were clearly different. The method can therefore be used to rapidly identify infections. Thus, this method can be used in outbreak situations where a particular amplitype has been identified and strains with this amplitype are multidrug-resistant. That is, in such cases the amplitype generated by this amplification procedure can be used as a surrogate marker for drug resistance before the results of standard susceptibility tests become available.

Identification of *M. tuberculosis* RFLP-type 021-2072 (strain W)

Figure 2:
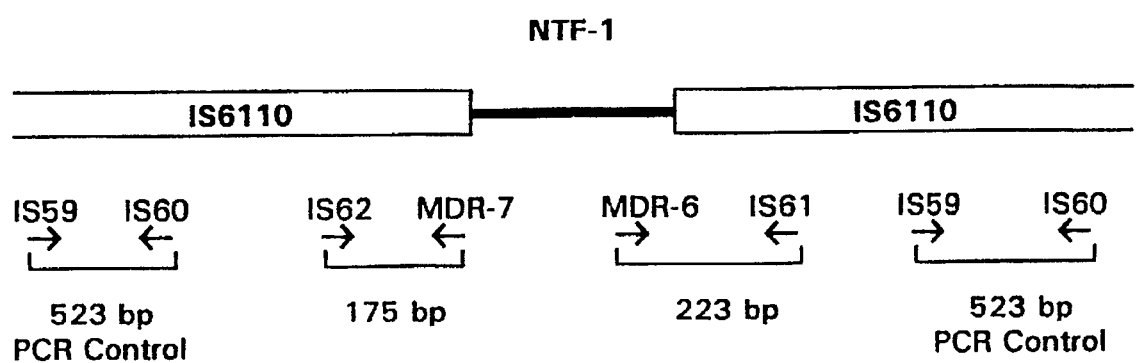
FIG. 2 shows multidrug-resistant M. tuberculosis: schematic representation of the 556 bp NTF-1 fragment between the IS6110 tandem repeat and the location of oligonucleotides used in PCR.

Polymerase chain reaction analysis of the flanking regions of IS6110 with primers specific for sequences at the 5' and 3' ends of IS6110 revealed a direct tandem repeat of IS6110 with an approximately 556 basepair intervening sequence in *M. tuberculosis* RFLP-type 021-2072 (FIG. 2). The location and orientation of this 556 bp fragment, designated NTF-1, was found to be specific for many multidrug-resistant strains of *M. tuberculosis* including RFLP-type 021-2072 and CDC strains listed previously. The NTF-1 sequence itself is not specific for multidrug-resistant strains, but is found in all *M. tuberculosis* tested Table 1. This orientation of the IS6110 direct tandem repeat and the NTF-1 spacer is the target of a multiplex PCR specific for multidrug-resistant strains of *M. tuberculosis*. This PCR detects the presence of a first junction, of the 3' end of the first IS6110 and the 5' end of NTF-1, and a second junction, of the 5' end of NTF-1 and the 3 end of the second IS6110. Additionally, this reaction has an internal PCR control, comprising two primers selected and oriented to amplify a region within IS6110, which product size is predictable.

The PCR mixture contained six primers which generate three amplicons from *M. tuberculosis* RFLP-type 021-2072: (1) 175 bp fragment generated by priming from the 3' end of IS6110 into the 5' end of NTF-1 (generated by the two primers set forth in SEQ. ID NOS: 7 and 9), (2) 223 bp fragment generated by priming from the 5' end of the IS6110 into the 3' end of NTF-1 (generated by the two primers set forth in SEQ ID NOS: 10 and 3), and (3) 523 bp fragment generated from within the IS6110 element (with the primers set forth in SEQ ID NOS: 11 and 12). The 175 bp fragment indicates the presence of the first junction, while the 223 bp fragment detects the presence of the second junction. The presence of both the 175 bp and 223 bp fragments indicate the presence of the NTF-1 sequence between the direct tandem repeat of IS6110, and the 523 bp fragment serves as an internal positive PCR control which should be present in all *M. tuberculosis* strains tested.

PCR was performed essentially as described earlier. The samples were amplified for 30 cycles with the following conditions: denaturation for 1.5 minutes at 94° C., annealing for 1.75 minutes at 60° C., and extension for 2.5 minutes at 72° C. A portion of the amplified mixture was removed and electrophoresed through a 2.0% agarose gel with molecular weight standards ranging from 100 to 1000 bp. The gel was stained with ethidium bromide and size of the bands of PCR products determined by comparison to both the molecular weight standards and the positive control. Strain 021-2072 produced three fragments, 175 bp, 223 bp and 523 bp.

A true positive result with the example primers for multidrug-resistant strains such as RFLP-type 021-2072 contains all three amplicons, and a true negative will contain at least the 523 bp fragment. Some strains have given rise to the 523 bp and 223 bp fragment or to fragments of varying size; these are considered negative. If the 523 bp internal positive control fragment is not amplified, the test is considered invalid and should be repeated.

Identification of Other Multidrug-Resistant *Mycobacterium tuberculosis*

The procedure described above for *M. tuberculosis* RFLP type 021-2072 was repeated for CDC strains 91-2870, 91-3006 (both of which have an identical PvuII RFLP pattern as Type 021-2072), 91-3378 and 91-2967 (each of which has a one or two band variation in PvuII RFLP pattern, i.e., have polymorphisms at a PvuII site). For each of these strains, three fragments were produced: 175 bp, 223 bp and 523 bp.

Throughout this application, various publications are referenced. The disclosures of these publications in their entireties are hereby incorporated by reference into this application in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims.

REFERENCES

1. Barnes, P. F., Bloch, A. B., Davidson, P. T. & Snider, Jr. D. E. (1991). Tuberculosis in patients with human immunodeficiency virus infection. *New England Journal of Medicine*, 324:1644–1650.
2. Cave, M. D., Eisenach, K. D., McDermott, P. F., Bates, J. H. & Crawford, J. T. (1991). IS6110: conservation of sequence in the *Mycobacterium tuberculosis* complex and its utilization in DNA fingerprinting. *Molecular and Cellular Probes* 5:73–80.
3. Dimri, G. P., Rudd, K. E., Morgan, M. K., Bayat, H. & Ferro-Luzzi Ames, G. (1992). Physical mapping of repetitive extragenic palindromic sequences in *Escherichia coli* and phylogenetic distribution among *Escherichia coli* strains and other enteric bacteria. *Journal of Bacteriology* 174:4583–4593.
4. Edlin, B. R., Tokars, J. I., Grieco, M. H., Crawford, J. T., Williams, J., Sordillo, E. M., Ong, K. R., Kilburn, J. O., Dooley, S. W., Castro, K. G., Jarvis, W. R. & Holmberg, S. D. (1992). An outbreak of multidrug-resistant tuberculosis among hospitalized patients with the acquired immunodeficiency syndrome. *New England Journal of Medicine* 326:1514–1521.
5. Greifinger, R. et al., (1992) MMWR, 41(28):507–509.
6. Hermans, P. W. M., van Soolingen, D. & van Embden, J. D. A. (1992). Characterization of a major polymorphic tandem repeat in *Mycobacterium tuberculosis* and its potential use in the epidemiology of *Mycobacterium kansasii* and *Mycobacterium gordonae*. *Journal of Bacteriology* 174:4157–4165.
7. M. A. Innis et al., eds. PCR Protocols: *A Guide to Methods and Applications* (1990), pp. 15–16, (Academic Press, Inc., San Diego).
8. Iovannisci, D. M. and Winn-Deen, E. S. (1993) Ligation amplification and fluorescence detection of *Mycobacterium tuberculosis* DNA, *Molecular and Cellular* Probes, 7:35–43.
9. Kent, B. B. & Kubica, K. G. P. (1985). *Public Health Mycobacteriology: A Guide for the Level III Laboratory*. U.S. Department of Health and Human Services, Centers for Disease Control, Atlanta, Ga. 207 pages.
10. Mullis, K. B. & Faloona, F.A. (1987). Specific synthesis of DNA in vitro via a polymerase-catalyzed chain reaction. *Methods in Enzymolology* 155:335–350.
11. Otal, I., Martin, C., Vincent-Levy-Frebault, V., Thierry, D. & Gicquel, B. (1991). Restriction fragment length polymorphism analysis using IS6110 as and epidemiological marker in tuberculosis. *Journal of Clinical Microbiology* 29:1252–1254.
12. Pearson, M. L., Jereb, J. A., Frieden, T. R., Crawford, J. T., Davis, B. J., Dooley, S. W. & Jarvis, W. R. (1992). Nosocomial transmission of multidrug-resistant *Mycobacterium tuberculosis*: a risk to patients and healthcare workers. *Annals of Internal Medicine* 117:191–196.
13. Plikaytis, B. B., Eisenach, K. D., Crawford, J. T. & Shinnick. T. M. (1991). Differentiation of *Mycobacterium tuberculosis* and *Mycobacterium bovis* by a polymerase chain reaction assay. *Molecular and Cellular Probes* 5:215–219.
14. Plikaytis, B. B., Plikaytis, B. D., Yakrus, M. A., Butler, W. R., Woodley, C. L, Silcox, V. A. & Shinnick T. M. (1992). Differentiation of slowly growing Mycobacterium species, including *Mycobacterium tuberculosis*, by gent amplification and restriction fragment length polymorphism analysis. *Journal Clinical Microbiology* 30:1815–822.
15. Sambrook et al., (1989) *Molecular Cloning: A Laboratory Manual*, 2nd Ed., Cold Spring Harbor Laboratory, Cold Spring Harbor, N.Y.
16. Shinnick, T. M. (1987). The 65-kilodalton antigen of *Mycobacterium tuberculosis*. Journal of Bacteriology 169:1080–1088.
17. Thierry, D., Cave, M.D., Eisenach, K. D., Crawford, J. T., Bates, J. H. Gicquel, B. & Guesdon, J. L (1990). 186110, and IS-like element of *Mycobacterium tuberculosis* complex. *Nucleic Acids Research* 18:188.
18. Versalovic, J., Koeuth, T., & Lupski, J. R. (1991). Distribution of repetitive DNA sequences in eubacteria and application to fingerprinting of bacterial genomes. *Nucleic Acids Research*. 19:6823–6831.
19. van Soolingen, et al., (1992). RFLP analysis of mycobacteria. Protocols MMB, National Institute of Public Health and Environmental Protection, Bilthoven,. Netherlands.
20. Wilson, K (1990). Preparation of Genomic DNA from Bacteria. Ausubel, F. M., Brent, R., Kinston, R. E., Moore, D. D., Seidman, I. G., Smith, J. A., and Struhl, K., eds. Current Protocols in Molecular Biology. Vol. 1. Green and Wiley-Interscience, New York. 2.4.1–2.4.2.
21. Wu, D. Y. and Wallace, R. B. (1989). The ligation amplification reaction (LAR)—Amplification of specific DNA sequences using sequential rounds of template- dependent ligation. *Genomics* 4:560–569.

What is claimed is:

1. A method of determining the presence of a multidrug-resistant *Mycobacterium tuberculosis* RFLP type 021-2072 in a sample, comprising detecting the presence of a 556 nucleotide DNA fragment between a direct tandem repeat of insertion element IS6110, the presence of the fragment between the repeat indicating the presence of the multidrug-resistant *Mycobacterium tuberculosis* in the sample.

2. The method of claim 1, wherein the presence of the fragment is detected by detecting the presence of a first unique junction between a first IS6110 element and the fragment and a second unique junction between the fragment and a second IS6110 element of the repeat.

3. The method of claim 2, wherein the detecting step comprises a) performing a polymerase chain reaction utilizing a first and second set of oligonucleotide primers,
   i) the first set comprising a first primer which specifically hybridizes to a region of IS6110 such that a polymerase chain reaction product synthesized from the first primer is synthesized toward the first junction and a second primer which specifically hybridizes to a region of the fragment such that a polymerase chain reaction product synthesized from the second primer is synthesized toward the first junction; and
   ii) the second set comprising a third primer which specifically hybridizes to a region of the fragment such that a polymerase chain reaction product synthesized from the third primer is synthesized toward the second junction and a fourth primer which specifically hybridizes to a region of IS6110 such that a polymerase chain reaction product synthesized from the fourth primer is synthesized toward the second junction;

b) determining the size of the polymerase chain reaction product; and c) the size of the polymerase chain reaction product having the 556 nucleotide DNA fragment between the direct tandem repeat of IS6110 indicating the presence of the multidrug-resistant *M. tuberculosis* in the sample.

4. The method of claim 2, wherein the detecting step comprises a) performing a ligase chain reaction utilizing a first and second set of oligonucleotide primers i) the first set comprising a first primer which specifically hybridizes to one strand of IS6110 immediately 5' to the first junction and a second primer which specifically hybridizes to the same strand of the fragment immediately 3' to the first junction such that a ligase chain reaction product can be formed with the two primers, and ii) the second set comprising a third primer which specifically hybridizes to one strand of the fragment immediately 5' to the second junction and a fourth primer which specifically hybridizes to the same strand of IS6110 immediately 3' to the second junction such that a ligase chain reaction product can be formed with the two primers;

b) determining the size of the ligase chain reaction product; and c) comparing the size of the ligase chain reaction product of each primer set with the additive size of the two primers comprising the primer set, a match in size indicating the presence of the first and second junctions.

5. The method of claim 3, further comprising a positive control test for the presence of *Mycobacterium tuberculosis*, utilizing a third set of oligonucleotide primers comprising a fifth primer which specifically hybridizes to a region of IS6110 and a sixth primer which specifically hybridizes to a second region of IS6110, such that a polymerase chain reaction product synthesized from the fifth primer is synthesized toward the sixth primer and a polymerase chain reaction product synthesized from the sixth primer is synthesized toward the fifth primer, wherein the production by polymerase chain reaction of a product of the fifth primer and the sixth primer indicates the presence of *Mycobacterium tuberculosis*.

6. The method of claim 3, wherein the first primer consists of the nucleotide sequence set forth in SEQ ID NO: 7.

7. The method of claim 3, wherein the second primer consists of the nucleotide sequence set forth in SEQ ID NO: 9.

8. The method of claim 3, wherein the third primer consists of the nucleotide sequence set forth in SEQ ID NO: 10.

9. The method of claim 3, wherein the fourth primer consists of the nucleotide sequence set forth in SEQ ID NO: 3.

10. The method of claim 5, wherein the fifth primer consists of the nucleotide sequence set forth in SEQ ID NO: 11.

11. The method of claim 5, wherein the sixth primer consists of the nucleotide sequence set forth in SEQ ID NO: 12.

12. A nucleic acid having the nucleotide sequence set forth in SEQ ID NO: 13.

13. A nucleic acid having the nucleotide sequence set forth in SEQ ID NO: 9.

14. A nucleic acid having the nucleotide sequence set forth in SEQ ID NO: 10.

* * * * *